United States Patent [19]

Takematsu et al.

[11] 4,272,283
[45] Jun. 9, 1981

[54] HERBICIDAL COMPOSITION AND METHOD FOR CONTROLLING WEEDS

[75] Inventors: Tetsuo Takematsu; Makoto Konnai, both of Utsunomiya; Kaoru Ikeda, Ami, all of Japan

[73] Assignee: Mitsubishi Petrochemical Co., Ltd., Japan

[21] Appl. No.: 49,641

[22] Filed: Jun. 18, 1979

[30] Foreign Application Priority Data

Jun. 20, 1978 [JP] Japan ............................ 53-73797

[51] Int. Cl.³ .................. A01N 43/40; A01N 43/36; A01N 37/18; A01N 43/00
[52] U.S. Cl. ........................................ 71/94; 71/88; 71/92; 71/95; 71/118; 71/120
[58] Field of Search ................... 71/88, 94, 95, 118

[56] References Cited

U.S. PATENT DOCUMENTS

| 3,134,666 | 5/1964 | McRae ................. | 71/118 |
| 3,382,280 | 5/1968 | Huffman ............... | 71/118 |
| 3,443,927 | 5/1969 | Unger .................. | 71/118 |
| 4,050,920 | 9/1977 | Takematsu et al. ..... | 71/118 |

FOREIGN PATENT DOCUMENTS 231263  3/1969  U.S.S.R. ................................ 71/88

OTHER PUBLICATIONS

Takematsu et al. I, "Herbicides", (1976), CA 86 No. 51581 y, (1977).

Primary Examiner—Glennon H. Hollrah
Attorney, Agent, or Firm—Wenderoth, Lind & Ponack

[57] ABSTRACT

A herbicidal composition comprising a herbicidal amount of a mixture of (a) at least one S-α,α-dimethylbenzyl-N-alkylenimine carbothiolate of the formula

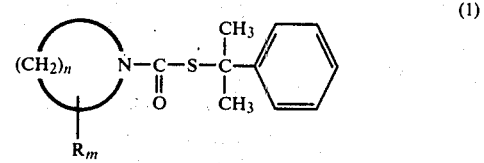

wherein R represents a lower alkyl group, m is 0, 1 or 2, n is 4, 5 or 6, and the chain of n —$CH_2$— linkages may contain one oxygen atom, and (b) at least one compound selected from the group consisting of N-[p-(p-chlorobenzyloxy)phenyl]-3,4,5,6-tetrahydrophthalimide, 1,3-dimethyl-4-(2,4-dichlorobenzoyl)-5-(p-tolylsulfonyloxy)pyrazole, 3,4-dichloropropionanilide, and 1-(2-phenylpropyl)-3-(4-tolyl)urea, and a method for controlling weeds, which comprises applying 1 to 2,000 g/10 ares of the aforesaid composition to the locus where the weeds are growing or will grow. The composition is especially useful in rice cultivation for controlling weeds of Family Gramineae (e.g., barnyard grass) and broad-leaved weeds without toxocity to rice.

7 Claims, No Drawings

HERBICIDAL COMPOSITION AND METHOD FOR CONTROLLING WEEDS

This invention relates to a herbicidal composition comprising a combination of certain known herbicidally active ingredients which can produce a unique synergistic effect, and to a method for controlling weeds.

Particularly, this invention relates to a herbicidal composition which exhibits a selective herbicidal effect among the genera of plants of Family Gramineae whereby it controls barnyard grass, a hazardous plant belonging to Family Gramineae, but is non-toxic to rice, a useful plant belonging to Family Gramineae; has a broad herbicidal spectrum against hazardous plants of Family Gramineae such as barnyard grass and broad-leaved weeds such as toothcup, narrowleaf waterplantain and red-root pigweed; shows satisfactory herbicidal effect at reduced rates of application with an extended period available for application, and which particularly shows a noteworthy herbicidal effect in rice cultivation; and to a method for controlling weeds.

More specifically, this invention relates to a herbicidal composition comprising a herbicidal amount of a mixture of (a) at least one S-α,α-dimethylbenzyl-N-alkylenimine carbothiolate of the following formula

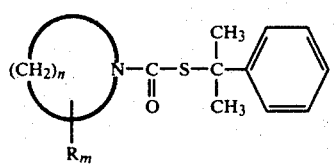

(1)

wherein R represents a lower alkyl group, m is 0, 1 or 2, n is 4, 5 or 6, and the chain of n —CH$_2$— linkages may contain one oxygen atom, and (b) at least one compound selected from the group consisting of N-[p-(p-chlorobenzyloxy)phenyl]-3,4,5,6-tetrahydrophthalimide, 1,3-dimethyl-4-(2,4-dichlorobenzoyl)-5-(p-tolylsulfonylpxy)pyrazole, 3,4-dichloropropionanilide and 1-(2-phenylpropyl)-3-(4-tolyl)urea.

Since the herbicidal composition of this invention exhibits an outstanding synergistic effect when used in rice cultivation, it will be described hereinbelow mainly with reference to rice cultivation as a typical example. It should be understood that the herbicidal composition of this invention is useful in controlling a wider range of other weeds.

The most troublesome weed in rice cultivation is barnyard grass which belongs to Family Gramineae. Barnyard grass looks very much like rice. It grows amidst rice plants, and is difficult to control. It has been the most important technical problem in rice cultivation to develop a herbicide and a herbicidal method which can selectively control barnyard grass without causing toxicity to rice which also belongs to Family Gramineae.

The practice of cultivating rice is classified into a transplantation method by which seedlings grown separately are transplanted in paddies, and a direct sowing method by which rice seeds are directly sown on paddies and grown there. Barnyard grass grows both in regions where the former cultivation method is practiced, such as Japan, Korea, Taiwan, China, Philippines, Thailand and Burma, and in regions where the latter cultivation method is practiced, such as United States, Brazil, Italy, Spain, India and Sri Lanka and a solution to the above technical problem has been desired. The latter practice of cultivation is labor-saving and less costly, and is expected to supersede the former practice. But when in the latter practice, a herbicide is applied to rice paddies during, or in the early stage after, emergence when barnyard grass is least resistant to the herbicide, phytotoxicity to rice plant is more serious than in the former cultivation practice because that period coincides with the period when the rice is least resistant to the herbicide. Accordingly, it may be said that the success of rice cultivation, especially by the direct sowing method, depends upon a herbicide and a herbicidal method which are nontoxic to rice plants and can effectively control barnyard grass and broad-leaved weeds.

When Benthiocarb or Molinate, now widely used for rice cultivation is aquatic paddies, is applied during, or in the early stage after, emergence of rice and barnyard grass, not only barnyard grass but also rice plants will be withered because such a herbicide shows no selectivity between them. Accordingly, efforts are being made to produce herbicidal selectivity in these herbicides by artificial means. For example, rice plants are grown to a stage when they become more resistant to the herbicides, and then transplanted into rice paddies where barnyard grass is in the stage of emergence or in the early stage after emergence, and the herbicides are applied to rice paddies at this stage.

Propanil, common name for 3,4-dichloropropionanilide) utilized in rice cultivation by a direct sowing method in dry paddies or in upland farms has a herbicidal action on barnyard grass with reduced toxicity to rice plants. But when it is applied to submerged paddies during emergence or in the early stage of growth, it rapidly undergoes hydrolysis, and does not show an appreciable herbicidal effect.

Accordingly, conventional herbicides utilized for rice cultivation cause phytotoxicity to rice plants when applied during, or in the early stage after, emergence at which time barnyard grass is least resistant to the herbicides. Or depending upon the mode of application, such a conventional herbicide may be decomposed to lose a herbicidal effect. In spite of impressing demand, a selective herbicide having a broad herbicidal spectrum which can control at low rates of application barnyard grass and broad-leaved weeds selectively and effectively without causing toxicity to rice plants has not been provided in the past.

The present inventors have made investigations in order to provide a herbicide which will meet the above demand. These investigations have led to the discovery that by using the known herbicide (a) of general formula (1) and the known herbicide (b) stated hereinabove, a novel unique synergistic effect can be achieved, and a herbicidal composition and a method for controlling weeds which meet the above demand can be provided.

The work of the inventors shows that the herbicide (a) exhibits a superior effect in controlling barnyard grass during the time ranging from emergence to the one-leaf stage when applied at a rate of not more than 50 g/10a, but its effect is insufficient in controlling barnyard grass in the two-leaf and later stages at the same rates, and that its controlling effect against broad-leaved weeds is relatively weak. It has also been found that N-[p-(p-chlorobenzyloxy)phenyl]-3,4,5,6-tetrahydrophthalimide (to be referred to as MK-129) or 1,3-dimethyl-4-(2,4-dichlorobenzoyl)-5-(p-tolylsulfonyloxy)pyrazole (to be referred to as SW-751), belonging to the herbicide (b), shows a relatively good controlling effect against broad-leaved weeds, but only an inferior control effect on barnyard grass, and that for such a herbicide to show a control effect against barnyard grass, it must be used in amounts which will cause marked phytotoxicity to rice plants (2 to 10 times the amount effective for controlling broad-leaved weeds).

When an amount of the herbicide (a) which will show a herbicidal effect of 80% to less than 95% on barnyard grass and not more than 10% on broad-leaved weeds is used in combination with an amount of MK-129 or SW-751, the herbicide (b), which will show no utilizable herbicidal effect on barnyard grass and broad-leaved weeds, a satisfactorily high selective herbicidal activity is unexpectedly exhibited against barnyard grass and broad-leaved weeds over a broad herbicidal spectrum at low rates of application without any phytotoxicity to rice plants.

It has also been found that a similar synergistic effect can be achieved by using the herbicide (a) in a similar amount in combination with an amount of 1-(2-phenylpropyl)-3-(4-tolyl)urea (to be abbreviated SK-223) as herbicide (b) which will show only an insufficient herbicidal effect on barnyard grass and broad-leaved weeds, or by using the herbicide (a) and 3,4-dichloropropionanilide as herbicide (b).

It is an object of this invention therefore to provide a herbicidal composition which shows the aforesaid unique synergistic effect.

Another object of this invention is to provide a method for controlling weeds which can achieve the aforesaid unique synergistic effect.

The above and other objects and advantages of this invention will become more apparent from the following description.

The herbicidally active ingredient (a) used in this invention is an S-α,α-dimethylbenzyl-N-alkylenimine carbothiolate of the formula

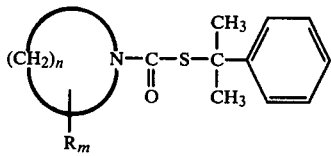

(1)

wherein R represents a lower alkyl group, preferably a linear or branched alkyl group having 1 to 4 carbon atoms, m is 0, 1 or 2, n is 4, 5 or 6, and the chain of n —CH$_2$— linkages may contain one oxygen atom with the proviso that no oxygen atom is present between —N— and the adjacent —CH$_2$—.

The compounds of formula (1) and a method for preparation thereof are disclosed in detail, for example, in Japanese Laid-Open Patent Publication No. 98331 published on Aug. 30, 1976.

Specific examples of the compound of formula (1) are listed below with abbreviations where applicable.

S-α,α-dimethylbenzyl-N-pyrrolidine carbothiolate (MUW-1192),

S-α,α-dimethylbenzyl-N-piperidine carbothiolate (MUW-1193),

S-α,α-dimethylbenzyl-N-hexamethylenimine carbothiolate (MUW-1138),

S-α,α-dimethylbenzyl-N-(2-methylpiperidine)-carbothiolate (MUW-1222),

S-α,α-dimethylbenzyl-N-morpholine carbothiolate (MUW-1194),

S-α,α-dimethylbenzyl-N-(2-methyl-5-ethylpiperidine) carbothiolate (MUW-2425),

S-α,α-dimethylbenzyl-N-(3-methylpiperidine) carbothiolate,

S-α,α-dimethylbenzyl-N-(4-methylpiperidine) carbothiolate,

S-α,α-dimethylbenzyl-N-(2-ethylpiperidine) carbothiolate,

S-α,α-dimethylbenzyl-N-(3-ethylpiperidine) carbothiolate,

S-α,α-dimethylbenzyl-N-(4-ethylpiperidine) carbothiolate,

S-α,α-dimethylbenzyl-N-(4-n-propylpiperidine) carbothiolate,

S-α,α-dimethylbenzyl-N-(4-iso-propylpiperidine) carbothiolate,

S-α,α-dimethylbenzyl-N-(4-n-butylpiperidine) carbothiolate,

S-α,α-dimethylbenzyl-N-(4-iso-butylpiperidine) carbothiolate,

S-α,α-dimethylbenzyl-N-(4-tert.-butylpiperidine) carbothiolate, and

S-α,α-dimethylbenzyl-N-(4-sec.-butylpiperidine) carbothiolate.

The other known herbicidally active ingredient (b) used in combination with the ingredient (a) is at least one compound selected from the group consisting of N-[p-(p-chlorobenzyloxy)phenyl]-3,4,5,6-tetrahydrophthalimide (abbreviated MK-129), 1,3-dimethyl-4-(2,4-dichlorobenzoyl)-5-(p-tolylsulfonyloxy)pyrazole (abbreviated SW-751), 3,4-dichloropropionanilide (common name: propanil), and 1-(2-phenylpropyl)-3-(4-tolyl)urea (abbreviated SK-223).

These compounds are available on the market, and methods for production thereof are disclosed, for example, in Japanese Laid-Open Patent Publications Nos. 48631/73 and 126830/75 and Japanese Patent Publication No. 53454/73.

The mixing proportions of the compound of formula (1) as the ingredient (a) and the ingredient (b) can be selected depending upon the combination of the ingredients, the conditions for application, the types of weeds to be controlled, and locus to which they are to be applied, and other factors. For example, 1 to 400 parts by weight of the ingredient (b) is used per 100 parts by weight of the ingredient (a). Specifically, when the ingredient (a) is used in combination with MK-129, the amount of MK-129 is preferably about 1 to about 50 parts by weight, more preferably about 2.5 to about 40 parts by weight, per 100 parts by weight of the ingredient (a). When the ingredient (a) is to be used together with propanil or SK-223, the amount of the propanil or SK-223 is preferably about 10 to about 400 parts by weight, more preferably about 10 to about 300 parts by weight, especially preferably about 50 to about 200 parts by weight, per 100 parts by weight of the ingredient (a). When the ingredient (a) is used together with SW-751, the amount of SW-751 is preferably about 50 to about 200 parts by weight, more preferably about 50 to about 100 parts by weight, per 100 parts by weight of the ingredient (a).

In addition to at least one ingredient (a) and at least one ingredient (b), the herbicidal composition of this invention may contain a conventional diluent or carrier. Examples of such a diluent or carrier include solid diluents or carriers such as diatomaceous earth, slaked lime, calcium carbonate, white carbon, kaolin, bentonite, Zeeklite, wood flour, nitrocellulose and starch; liquid diluents or carriers such as benzene, toluene, xylene, solvent naphtha, dioxane, isophorone, methylisobutyl ketone, dimethylformamide and dimethylsulfoxide; and gaseous diluents or carriers such as vinyl chloride, carbon dioxide, Freon, propane and butane. To increase the suspendability or emulsifiability of the herbicidal composition, a solid or liquid surface-active agent may be used. Examples of the surfactant are sodium alkylphosphates, sodium alkylbenzenesulfonates, sodium ligninsulfonate, polyoxyethylene lauryl ether, polyoxyethylene alkylaryl ethers and polyoxyethylene sorbitan fatty acid esters.

The herbicidal composition of this invention may further contain another agricultural or horticultural chemical such as another herbicide, a fertilizer, a growth regulator, an insecticide, a fungicide or a nematocide.

The herbicidal composition of this invention may be in various forms such as wettable powders, emulsifiable concentrates, granules, dusts, oils or aerosols. The contents of the active ingredients in the various formulations of the herbicidal composition of this invention can be selected and changed as desired. For example, the total amount of the ingredients (a) and (b) is about 0.01 to about 100%, preferably about 1 to about 95%, based on the weight of the herbicidal composition.

According to this invention, there is provided a method for controlling weeds, which comprises applying a herbicidal amount of a mixture of the ingredients (a) and (b) to the locus where the weeds are growing or will grow.

The application may be done in the pre-emergence stage or in the post-emergence stage by any desired means. For example, the herbicidally active ingredients (a) and (b) may be applied by using a duster, granule applicator or sprayer by various means such as soil treatment, soil incorporation treatment, soil fumigation treatment, or contact treatment.

The rate of application can be properly chosen according to the weeds to be controlled, the time of application, the place of application, etc. For example, the rate of application is 1 to 2,000 g/10 ares, preferably 10 to 1,500 g/10 ares, more preferably 25 to 1,000 g/10 ares.

The herbicidal composition of this invention is especially superior for controlling weeds in the cultivation of rice plants both in upland farms and in aquatic paddies. Hence, the method of this invention is especially suitable for controlling weeds in rice cultivation.

Examples of the weeds that can be controlled by the composition and method of this invention include barnyard grass (*Echinochloa crus-galli*), toothcup (*Rotala indica*), narrowleaf waterplantain (*Alisma canaliculatum*), Cyperus sp. (*Cyperus globosus*), Sagittaria pygmaea, hard-stem bulrush (*Scirpus juncoides*), Lindernia sp., red-root pigweed (*Amaranthus retroflexus*), Vandellia sp., goose grass (*Eleusin indica*), and crabgrass (*Digitaria sanguinalis*).

The herbicidal composition of this invention is especially suitable for controlling weeds in the cultivation of rice plants by a direct sowing method. Accordingly, the present invention can provide a herbicidal composition and a method of controlling weeds in the cultivation of rice plants by a direct sowing method.

The following examples illustrate the present invention in greater detail. In these examples, all parts are by weight unless otherwise specified.

FORMULATION EXAMPLE 1

| | |
|---|---|
| MUW 1193 | 10 parts |
| MK-129 | 2 parts |
| 2:1 mixture of talc and clay | 83 parts |
| Sodium alkylbenzenesulfonate | 3 parts |
| Sodium dinaphthylmethanesulfonate | 2 parts |

The above ingredients were mixed and pulverized to form a wettable powder.

FORMULATION EXAMPLE 2

| | |
|---|---|
| MUW 1138 | 7 parts |
| MK-129 | 1 part |
| 1:1 mixture of talc and clay | 87 parts |
| Sodium ligninsulfonate | 3 parts |
| Sodium dodecylbenzenesulfonate | 2 parts |

The above ingredients were mixed and pulverized well, and granulated in a customary manner by a granulator.

FORMULATION EXAMPLE 3

| | |
|---|---|
| MUW 1139 | 10 parts |
| SW-751 | 5 parts |
| Zeeklite | 80 parts |
| Sorpol 800 (registered trademark | 3 parts |
| Alkyllaurylsulfonate | 2 parts |

The above ingredients were mixed and pulverized to form a wettable powder.

FORMULATION EXAMPLE 4

| | |
|---|---|
| MUW 1138 | 10 parts |
| Propanil | 10 parts |
| Clay | 50 parts |
| Zeeklite | 25 parts |
| Sodium ligninsulfonate | 3 parts |
| Sodium alkylbenzenesulfonate | 2 parts |

The above ingredients were mixed and pulverized to form a wettable powder.

FORMULATION EXAMPLE 5

| | | |
|---|---|---|
| MUW 1138 | 7 | parts |
| SK-223 | 7 | parts |
| MK-129 | 1.5 | parts |
| 1:1 mixture of talc and clay | 78 | parts |
| Sodium ligninsulfonate | 3 | parts |
| Sodium dodecylbenzenesulfonate | 3.5 | parts |

The above ingredients were mixed and pulverized, and then granulated in a customary manner by a granulator.

FORMULATION EXAMPLE 6

| MUW 1138   | 18 parts |
| Propanil   | 36 parts |
| Xylene     | 40 parts |
| Sorpol 800A | 6 parts |

The above ingredients were mixed to form an emulsifiable concentrate in which the ratio of the amount of propanil to MUW 1138 was 2:1.

FORMULATION EXAMPLE 7

| MUW 1193 | 10 parts |
| SK-223   | 15 parts |
| Xylene   | 65 parts |
| Sorpol 800 | 10 parts |

The above ingredients were mixed to form an emulsifiable concentrate.

FORMULATION EXAMPLE 8

| MUW 1193 | 20 parts |
| SW-751   | 10 parts |
| Xylene   | 60 parts |
| Sorpol 800 | 10 parts |

The above ingredients were mixed to form an emulsifiable concentrate.

WEED CONTROL EXAMPLE 1

Test in a submerged condition on the use of the ingredient (a) and MK-129 either alone or in admixture:

Pots each having an inside diameter of 12 cm were filled with paddy soil, and seeds of barnyard grass, toothcup and narrowleaf waterplantain were sown. Rince plants (variety: "Koshihikari") in the two-leaf stage were transplanted in each pot. Rice seeds immediately after emergence were sown in each pot. The pots were submerged to a depth of 3 cm, and kept in a greenhouse. Upon emergence of barnyard grass seeds, a water-diluted wettable powder of the chemicals shown in Table 1 was applied to each pot in the dosages shown in Table 1. The plants were grown for 30 days in the greenhouse. Then, the control activities of the chemicals on each type of weeds and the phytotoxicities of the chemicals were examined. The herbicidal activities were evaluated on the scale of 0 to 5, and the phytotoxicities to rice, of − to +++, as indicated below. The results are shown in Table 1.

Herbicidal activity (the control ratio based on a non-treated lot);
5: at least 95%
4: 80% to less than 95%
3: 50% to less than 80%
2: 30% to less than 50%
1: 11% to less than 30%
0: less than 11%
Degree of phytotoxicity to rice:
−: No phytotoxicity
±: Very slight
+: Slight
++: Moderate
+++: Severe These evaluations are the same throughout the following Weed Control Examples. In the following tables, the Run Nos. are preceded by I, which stands for "invention", or C, which stands for "comparison".

TABLE 1

| Run No. | Compounds | Dosage g 10a | Herbicidal activity Barnyard grass | Toothcup | Narrowleaf waterplantain | Phytotoxicity to rice Direct sowing | Transplantation |
|---|---|---|---|---|---|---|---|
| C1 | MUW 1193 | 50 | 4.5 | 1 | 0 | — | — |
|    |          | 25 | 4   | 0 | 0 | — | — |
| C2 | MUW 1138 | 50 | 4.5 | 1 | 0 | — | — |
|    |          | 25 | 4   | 0 | 0 | — | — |
| C4 | MK-129   | 5   | 0   | 3.5 | 3 | — | — |
|    |          | 2.5 | 0   | 2 | 1.5-2 | — | — |
| I1 | MUW 1138 + MK-129 | 50 + 5 | 5 | 5 | 5 | — | — |
|    |          | 50 + 2.5 | 5 | 5 | 5 | — | — |
|    |          | 25 + 5 | 5 | 5 | 4.5 | — | — |
|    |          | 25 + 2.5 | 5 | 5 | 4 | — | — |
| I2 | MUW 1193 + MK-129 | 50 + 5 | 5 | 5 | 5 | — | — |
|    |          | 50 + 2.5 | 5 | 5 | 5 | — | — |
|    |          | 25 + 5 | 5 | 5 | 5 | — | — |
|    |          | 25 + 2.5 | 5 | 5 | 5 | — | — |
| C4 | MUW 1194 | 50 | 4-4.5 | 2 | 0 | — | — |
|    |          | 25 | 4 | 1 | 0 | — | — |
|    |          | 12.5 | 2 | 0 | 0 | — | — |
| C5 | MUW 1222 | 50 | 4-4.5 | 1 | 0 | — | — |
|    |          | 25 | 4 | 1 | 0 | — | — |
|    |          | 12.5 | 2 | 0 | 0 | — | — |
| C6 | MUW 2425 | 50 | 4 | 1.5 | 0 | — | — |
|    |          | 25 | 4 | 1 | 0 | — | — |
|    |          | 12.5 | 2 | 0 | 0 | — | — |
| I3 | MUW 1194 + MK-129 | 50 + 5 | 5 | 5 | 5 | — | — |
|    |          | 50 + 2.5 | 5 | 5 | 5 | — | — |
|    |          | 25 + 5 | 5 | 5 | 5 | — | — |
|    |          | 25 + 2.5 | 5 | 5 | 5 | — | — |
|    |          | 12.5 + 5 | 5 | 5 | 4.5 | — | — |
|    |          | 12.5 + 2.5 | 5 | 5 | 4.5 | — | — |
| I4 | MUW 1222 + MK-129 | 50 + 5 | 5 | 5 | 5 | — | — |
|    |          | 50 + 2.5 | 5 | 5 | 5 | — | — |
|    |          | 25 + 5 | 5 | 5 | 5 | — | — |
|    |          | 25 + 2.5 | 5 | 5 | 5 | — | — |

TABLE 1-continued

| Run No. | Compounds | Dosage g 10a | Herbicidal activity | | | Phytotoxicity to rice | |
|---|---|---|---|---|---|---|---|
| | | | Barnyard grass | Toothcup | Narrowleaf waterplantain | Direct sowing | Transplantation |
| | MK-129 | 12.5 + 5 | 5 | 5 | 4.5 | — | — |
| | | 12.5 + 2.5 | 5 | 4.5 | 4 | — | — |
| | | 50 + 5 | 5 | 5 | 5 | — | — |
| | | 50 + 2.5 | 5 | 5 | 5 | — | — |
| | MUW 2425 | 25 + 5 | 5 | 5 | 5 | — | — |
| I5 | + | 25 + 2.5 | 5 | 5 | 4.5 | — | — |
| | MK-129 | 12.5 + 5 | 5 | 5 | 4.5 | — | — |
| | | 12.5 + 2.5 | 5 | 4.5 | 4.5 | — | — |
| | Non-treated (control) | | 0 | 0 | 0 | — | — |

WEED CONTROL EXAMPLE 2

Test in a submerged condition on the use of the ingredient (a) and MK-129 either alone or in admixture:

The same procedure as in Weed Control Example 1 was repeated except that the dosages of application were changed as shown in Table 2. The results are shown in Table 2.

WEED CONTROL EXAMPLE 3

Test in a submerged condition on the use of the ingredient (a) and SW-751 either alone or in admixture:

The same procedure as in Weed Control Example 1 was repeated using weeds shown in Table 3. The results are shown in Table 3.

TABLE 2

| Run No. | Compounds | Dosage g 10a | Herbicidal activity | | | Phytotoxicity to rice | |
|---|---|---|---|---|---|---|---|
| | | | Barnyard grass | Toothcup | Narrowleaf waterplantain | Direct sowing | Transplantation |
| C8 | MUW 1193 | 100 | 5 | 2.5 | 1 | — | — |
| C9 | MUW 1138 | 100 | 5 | 2 | 0 | — | — |
| C10 | MK-129 | 5 | 0 | 3.5 | 3 | — | — |
| | | 2.5 | 0 | 2 | 1.5–2 | — | — |
| | MUW 1138 | 100 + 5 | 5 | 5 | 5 | — | — |
| I6 | + | 100 + 2.5 | 5 | 5 | 5 | — | — |
| | MK-129 | | | | | | |
| | MUW 1193 | 100 + 5 | 5 | 5 | 5 | — | — |
| I7 | + | 100 + 2.5 | 5 | 5 | 5 | — | — |
| | MK-129 | | | | | | |
| C11 | MUW 1194 | 100 | 5 | 3–3.5 | 1 | — | — |
| C12 | MUW 1222 | 100 | 5 | 2 | 0 | — | — |
| C13 | MUW 2425 | 100 | 5 | 2 | 0 | — | — |
| C14 | MK-129 | 5 | 0 | 3.5 | 3 | — | — |
| | | 2.5 | 0 | 2 | 1.5–2 | — | — |
| | MUW 1194 | 100 + 5 | 5 | 5 | 5 | — | — |
| I8 | + | 100 + 2.5 | 5 | 5 | 5 | — | — |
| | MK-129 | | | | | | |
| | MUW 1222 | 100 + 5 | 5 | 5 | 5 | — | — |
| I9 | + | 100 + 2.5 | 5 | 5 | 5 | — | — |
| | MK-129 | | | | | | |
| | MUW 2425 | 100 + 5 | 5 | 5 | 5 | — | — |
| I10 | + | 100 + 2.5 | 5 | 5 | 5 | — | — |
| | MK-129 | | | | | | |
| | Non-treated (control) | | 0 | 0 | 0 | — | — |

TABLE 3

| Compound | Dosage g 10a | Herbicidal activity | | | | | Phytotoxicity to rice | |
|---|---|---|---|---|---|---|---|---|
| | | Barnyard grass | Toothcup | Sagittaria pygmaea | Narrowleaf waterplantain | Cyperus sp. | Direct sowing | Transplantation |
| MUW 1138 | 50 | 4.5 | 1.5 | 0 | 0 | 1 | — | — |
| (comparison) | 25 | 4 | 0 | 0 | 0 | 0 | — | — |
| SW-751 | 80 | 4 | 3.5 | 3.5–4 | 2.5 | 2.5 | — | — |
| (comparison) | 40 | 3 | 1.5–2 | 2.5 | 1 | 1 | — | — |
| | 20 | 1.5–2 | 1.5 | 1.5 | 0 | 0 | — | — |
| MUW 1138 | 50 + 40 | 5 | 4 | 4 | 2.5–3 | 5 | — | — |
| + | 50 + 20 | 5 | 2.5–3 | 4 | 2.5 | 4.5–5 | — | — |
| SW-751 | 25 + 40 | 5 | 2.5 | 2.5–3 | 2 | 4.5 | — | — |
| (invention) | 25 + 20 | 5 | 1.5–2 | 2.5 | 1.5 | 4.5 | — | — |

TABLE 3-continued

| Compound | Dosage g 10a | Herbicidal activity | | | | | Phytotoxicity to rice | |
|---|---|---|---|---|---|---|---|---|
| | | Barnyard grass | Toothcup | Sagittaria pygmaea | Narrowleaf waterplantain | Cyperus sp. | Direct sowing | Transplantation |
| MUW 1193 | 50 | 4.5–5 | 2 | 0 | 0 | 1.5 | — | — |
| (comparison) | 25 | 4 | 0 | 0 | 0 | 0 | — | — |
| MUW 1193 | 50 + 40 | 5 | 4.5 | 4.5 | 4 | 5 | — | — |
| + | 25 + 40 | 5 | 3 | 4 | 3 | 4.5 | — | — |
| SW-751 | 50 + 20 | 5 | 3 | 4 | 3.5 | 4.5–5 | — | — |
| (invention) | 25 + 20 | 5 | 3 | 3 | 3 | 4.5 | — | — |
| MUW 1194 | 50 | 4–4.5 | 2 | 0 | 0 | 2 | — | — |
| (comparison) | 25 | 4 | 1 | 0 | 0 | 0 | — | — |
| MUW 1222 | 50 | 4–4.5 | 1 | 0 | 0 | 1.5 | — | — |
| (comparison) | 25 | 4 | 1 | 0 | 0 | 0 | — | — |
| MUW 2425 | 50 | 4 | 1.5 | 0 | 0 | 1.5 | — | — |
| (comparison) | 25 | 4 | 1 | 0 | 0 | 1 | — | — |
| MUW 1194 | 50 + 40 | 5 | 4.5 | 4 | 3 | 5 | — | — |
| + | 25 + 40 | 5 | 3 | 4 | 2 | 4.5–5 | — | — |
| SW-751 | 50 + 20 | 5 | 3.5 | 3.5–4 | 2.5 | 4.5 | — | — |
| (invention) | 25 + 20 | 5 | 2.5 | 3 | 2 | 4 | — | — |
| MUW 1222 | 50 + 40 | 5 | 4 | 4 | 3 | 4.5 | — | — |
| + | 25 + 40 | 5 | 2.5 | 4 | 2.5 | 4.5 | — | — |
| SW-751 | 50 + 20 | 5 | 2.5 | 3.5 | 2.5 | 4.5 | — | — |
| (invention) | 25 + 20 | 5 | 2 | 3 | 2 | 4 | — | — |
| MUW 2425 | 50 + 40 | 5 | 4.5 | 4.5 | 4 | 5 | — | — |
| + | 25 + 40 | 5 | 3 | 4 | 3 | 4.5 | — | — |
| SW-751 | 50 + 20 | 5 | 3.5 | 4 | 3.5 | 4.5 | — | — |
| (invention) | 25 + 20 | 5 | 3 | 3 | 3 | 4 | — | — |
| MUW 1138 (comparison) | 100 | 5 | 2 | 0 | 0 | 2.5 | — | — |
| SW-751 | 80 | 4 | 3.5 | 3.5–4 | 2.5 | 2.5 | — | — |
| (comparison) | 40 | 3 | 1.5–2 | 2.5 | 1 | 1 | — | — |
| | 20 | 1.5–2 | 1.5 | 1.5 | 0 | 0 | — | — |
| MUW 1138 | 100 + 40 | 5 | 5 | 5 | 5 | 5 | — | — |
| + | 100 + 20 | 5 | 5 | 4.5 | 4.5 | 5 | — | — |
| SW-751 (invention) | | | | | | | | |
| MUW 1192 (comparison) | 100 | 5 | 2.5 | 0 | 0 | 2.5 | — | — |
| MUW 1193 | 100 + 40 | 5 | 5 | 5 | 4 | 5 | — | — |
| + | 100 + 20 | 5 | 4 | 4.5 | 4 | 5 | — | — |
| SW-751 (invention) | | | | | | | | |
| MUW 1194 (comparison) | 100 | 5 | 3–3.5 | 0 | 1 | 2.5 | — | — |
| MUW 1222 (comparison) | 100 | 5 | 2 | 0 | 0 | 2.5 | — | — |
| MUW 2425 (comparison) | 100 | 5 | 2 | 0 | 0 | 2 | — | — |
| MUW 1194 | 100 + 40 | 5 | 5 | 5 | 4 | 5 | — | — |
| + | 100 + 20 | 5 | 5 | 4 | 3 | 5 | — | — |
| SW-751 (invention) | | | | | | | | |
| MUW 1222 | 100 + 40 | 5 | 5 | 5 | 4 | 5 | — | — |
| + | 100 + 20 | 5 | 4 | 4 | 3 | 5 | — | — |
| SW-751 (invention) | | | | | | | | |
| MUW 2425 | 100 + 40 | 5 | 5 | 5 | 4 | 5 | — | — |
| + | 100 + 20 | 5 | 4 | 4.5 | 4 | 5 | — | — |
| SW-751 (invention) | | | | | | | | |
| Non-treated | | 0 | 0 | 0 | 0 | 0 | — | — |

WEED CONTROL EXAMPLE 4

Test for soil treatment and foliar contact treatment using MUW 1138, MUW 1192, MUW 1193, MUW 1194, MUW 1222, MUW 2425 and propanil either alone or in admixture:

Pots each having an inside diameter of 12 cm were filled with the soil of an upland farm. Seeds of rice (variety: "Nipponbare"), barnyard grass, crabgrass and redroot pigweed were sown in a half (referred to as section A) of each pot, and grown for 15 days in a greenhouse. Then, seeds of the above four kinds of plants were sown in the remaining half (referred to as section B) of each pot. Two days after the second sowing, each of propanil and the compounds of formula (1) alone, or a mixture of propanil and each of the compounds of general formula (1) was applied at a rate of 2 ml per pot. Specifically, 1 ml of such a chemical was applied to the leaves and stalks of the plants growing in section A of the pot, and 1 ml of the chemical, to the soil in section B of the pot. The plants were grown for about 16 days, and the ability of each chemical to treat the leaves and stalks of the weeds and to treat the soil was examined. The evaluations were made in accordance with the criteria shown in Weed Control Example 1. The results are shown in Table 4.

It is seen from the results shown in Table 4 that the synergistic effect of propanil and the compound of formula (1) was outstanding on red-root pigweed. It is also noted from Table 4 that the herbicidal compositions of this invention have a broad herbicidal spectrum, and weeds in any stage of growth from emergence to active growth can be simultaneously withered by the same treatment. Hence, the herbicidal compositions of this invention have a very broad range of applicable periods.

In Table 4 and subsequent tables, L stands for the leaf stage.

house. When the rice and barnyard grass were in the 2.5-leaf stage, the toothcup was in the 1.5-leaf stage and the waterplantain was in the 3-leaf stage, the pots were each submerged to a depth of 4 cm. Each of the pots was then treated with each of the chemicals indicated in Table 5. Then, the plants were grown for about two weeks in a greenhouse, and the herbicidal activities on each of the weeds and the phytotoxicities to rice were examined, and evaluated in accordance with the criteria shown in Weed Control Example 1. The results are shown in Table 5.

It is seen from Table 5 that the synergistic effect of

TABLE 4

| Compound | Concentration ppm | Ability with soil treatment (at emergence) | | | | Ability with foliar and stalk treatment (in the growing stage) | | | |
|---|---|---|---|---|---|---|---|---|---|
| | | Barnyard grass | Crabgrass | Red-root pigweed | Rice | Barnyard grass (2.5-3L) | Crabgrass (3L) | Red-root pigweed (3.5L) | Rice (3.5L) |
| MUW 1138 | 2000 | 5 | 5 | 1.5 | — | 1.5 | 2 | 0 | — |
| (comparison) | 1000 | 4.5 | 5 | 0 | — | 0 | 1 | 0 | — |
| | 500 | 4 | 4.5 | 0 | — | 0 | 0 | 0 | — |
| MUW 1193 | 2000 | 5 | 5 | 2 | — | 1.5 | 2 | 0 | — |
| (comparison) | 1000 | 4.5 | 5 | 1 | — | 0 | 1.5 | 0 | — |
| | 500 | 4.5 | 5 | 0 | — | 0 | 0 | 0 | — |
| Propanil | 3000 | 0 | 0 | 0 | — | 5 | 5 | 5 | — |
| (comparison) | 2000 | 0 | 0 | 0 | — | 4 | 4.5 | 4.5 | — |
| | 1000 | 0 | 0 | 0 | — | 2.5-3 | 3.5 | 4 | — |
| MUW 1138 | 1000 + 2000 | 5 | 5 | 4.5 | — | 5 | 5 | 5 | — |
| + | 1000 + 1000 | 5 | 5 | 3.5 | — | 5 | 5 | 5 | — |
| propanil | 500 + 2000 | 5 | 5 | 4.5 | — | 5 | 5 | 5 | — |
| (invention) | 500 + 1000 | 4.5 | 4.5-5 | 3.5 | — | 5 | 5 | 5 | — |
| MUW 1193 | 1000 + 2000 | 5 | 5 | 4.5 | — | 5 | 5 | 5 | — |
| + | 1000 + 1000 | 5 | 5 | 4.5 | — | 5 | 5 | 5 | — |
| propanil | 500 + 2000 | 5 | 5 | 4-4.5 | — | 5 | 5 | 5 | — |
| (invention) | 500 + 1000 | 5 | 5 | 4-4.5 | — | 5 | 5 | 5 | — |
| MUW 1192 | 2000 | 5 | 5 | 1.0 | — | 1.5 | 2 | 0 | — |
| (comparison) | 1000 | 4.5 | 5 | 0 | — | 0 | 1 | 0 | — |
| | 500 | 4 | 4.5 | 0 | — | 0 | 0 | 0 | — |
| MUW 1194 | 2000 | 5 | 5 | 0 | — | 1 | 2 | 0 | — |
| (comparison) | 1000 | 4-4.5 | 5 | 0 | — | 0 | 1.5 | 0 | — |
| | 500 | 4 | 4 | 0 | — | 0 | 0 | 0 | — |
| MUW 1222 | 2000 | 5 | 5 | 1.5 | — | 1.5 | 1.5-2 | 0 | — |
| (comparison) | 1000 | 4.5 | 5 | 1 | — | 0 | 1 | 0 | — |
| | 500 | 4 | 4-4.5 | 0 | — | 0 | 0 | 0 | — |
| MUW 2425 | 2000 | 5 | 5 | 1.5 | — | 1-1.5 | 2 | 0 | — |
| (comparison) | 1000 | 4.5 | 5 | 1 | — | 0 | 0 | 0 | — |
| | 500 | 4 | 4-4.5 | 0 | — | 0 | 0 | 0 | — |
| MUW 1192 | 1000 + 2000 | 5 | 5 | 4.5 | — | 5 | 5 | 5 | — |
| + | 1000 + 1000 | 5 | 5 | 4 | — | 5 | 5 | 5 | — |
| propanil | 500 + 2000 | 4.5-5 | 5 | 4.5 | — | 5 | 5 | 5 | — |
| (invention) | 500 + 1000 | 4.5 | 4.5-5 | 3.5 | — | 5 | 5 | 5 | — |
| MUW 1194 | 1000 + 2000 | 5 | 5 | 4.5 | — | 5 | 5 | 5 | — |
| + | 1000 + 1000 | 5 | 5 | 4.5 | — | 5 | 5 | 5 | — |
| propanil | 500 + 2000 | 4.5 | 5 | 4 | — | 5 | 5 | 5 | — |
| (invention) | 500 + 1000 | 4-4.5 | 4.5 | 3.5 | — | 5 | 5 | 5 | — |
| MUW 1222 | 1000 + 2000 | 5 | 5 | 5 | — | 5 | 5 | 5 | — |
| + | 1000 + 1000 | 5 | 5 | 4.5 | — | 5 | 5 | 5 | — |
| propanil | 500 + 2000 | 4.5 | 5 | 4.5 | — | 5 | 5 | 5 | — |
| (invention) | 500 + 1000 | 4.5 | 4.5-5 | 4 | — | 5 | 5 | 5 | — |
| MUW 2425 | 1000 + 2000 | 5 | 5 | 4.5 | — | 5 | 5 | 5 | — |
| + | 1000 + 1000 | 5 | 5 | 4.5 | — | 5 | 5 | 5 | — |
| propanil | 500 + 2000 | 4.5-5 | 5 | 4 | — | 5 | 5 | 5 | — |
| (invention) | 500 + 1000 | 4.5 | 4.5-5 | 4 | — | 5 | 5 | 5 | — |
| Non-treated | | 0 | 0 | 0 | — | 0 | 0 | 0 | — |

WEED CONTROL EXAMPLE 5

Test for treatment in the active growing stage in a submerged condition using MUW 1138, MUW 1193 and propanil singly or a mixture of MUW 1138 and propanil and a mixture of MUW 1193 and propanil:

Pots each having an inside diameter of 12 cm were filled with the soil of aquatic paddy, and seeds of rice, barnyard grass, toothcup, and narrowleaf waterplantain immediately after emergence were scattered on the soil. The pots were each submerged to a depth of 1 cm, and these plants were grown for about 10 days in a greenthe compound of formula (1) and propanil was especially great on toothcup and narrowleaf waterplantain.

TABLE 5

| Compound | Dosage g 10a | Herbicidal activity | | | Phytotoxicity to rice (direct sowing 2.5L) |
|---|---|---|---|---|---|
| | | Barnyard grass (2.5L) | Toothcup (1.5L) | Narrowleaf waterplantain (3L) | |
| MUW 1138 | 200 | 4 | 1.5 | 1.5 | — |
| (comparison) | 100 | 3.5–4 | 0 | 1 | — |
| | 50 | 3.5 | 0 | 0 | — |
| MUW 1193 | 200 | 4 | 1–1.5 | 1 | — |
| (comparison) | 100 | 3.5–4 | 0 | 0.5 | — |
| | 50 | 3 | 0 | 0 | — |
| Propanil | 400 | 1.0 | 1.5 | 0 | — |
| (comparison) | 200 | 0 | 0 | 0 | — |
| | 100 | 0 | 0 | 0 | — |
| MUW 1138 | 200 + 400 | 5 | 5 | 5 | — |
| + | 100 + 400 | 5 | 5 | 5 | — |
| propanil | 200 + 200 | 5 | 5 | 5 | — |
| (invention) | 100 + 200 | 5 | 5 | 4.5 | — |
| MUW 1193 | 200 + 400 | 5 | 5 | 5 | — |
| + | 100 + 400 | 5 | 5 | 5 | — |
| propanil | 200 + 200 | 5 | 5 | 4.5 | — |
| (invention) | 100 + 200 | 5 | 4.5 | 4 | — |
| Non-treated | | 0 | 0 | 0 | — |

WEED CONTROL EXAMPLE 6

Test for soil treatment in a submerged condition using MUV 1138, SK-223 and MK-129 alone, a mixture of MUW 1138 and SK-223 or MK-129, and a mixture of MUW 1138, SK-223 and MK-129:

The same procedure as in Weed Control Example 1 was repeated using barnyard grass, toothcup, narrowleaf waterplantain, Cyperus sp. and hard-stem bulrush as weeds. The results are shown in Table 6. The synergistic effects of the mixtures on all these weeds were noted.

TABLE 6

| Compound | Dosage g 10a | Herbicidal activity | | | | | Phytotoxicity to rice | |
|---|---|---|---|---|---|---|---|---|
| | | Barnyard grass | Toothcup | Narrowleaf waterplantain | Cyperus sp. | Hard-stem bulrush | Direct sowing | Transplantation |
| MUW 1138 | 50 | 4.5 | 1 | 0 | 1 | 0 | — | — |
| (comparison) | 25 | 4 | 0 | 0 | 0 | 0 | — | — |
| SK-223 | 200 | 1.5 | 0 | 0 | 4.5 | 4.5 | — | — |
| (comparison) | 100 | 0 | 0 | 0 | 4 | 3.5 | — | — |
| | 50 | 0 | 0 | 0 | 3 | 3 | — | — |
| MK-129 | 10 | 0 | 4 | 4.5 | 4 | 2 | — | — |
| (comparison) | 5 | 0 | 3.5 | 3 | 3 | 1 | — | — |
| | 2.5 | 0 | 2 | 1.5–2 | 2 | 0 | — | — |
| MUW 1138 | 50 + 100 | 5 | 2.5–3 | 1.5–2 | 5 | 5 | — | — |
| + | 50 + 50 | 5 | 2.5 | 1.5–2 | 5 | 5 | — | — |
| SK-223 | 25 + 100 | 5 | 2.5 | 1.5 | 5 | 5 | — | — |
| (invention) | 25 + 50 | 5 | 2.5 | 1.5 | 5 | 5 | — | — |
| MNW 1138 | 50 + 5 | 5 | 5 | 5 | 4 | 2.5 | — | — |
| + | 50 + 2.5 | 5 | 5 | 5 | 3 | 1 | — | — |
| MK-129 | 25 + 5 | 5 | 5 | 4.5–5 | 4 | 2 | — | — |
| (invention) | 25 + 2.5 | 5 | 4.5–5 | 4 | 3 | 1 | — | — |
| | 50 + 100 + 5 | 5 | 5 | 5 | 5 | 5 | — | — |
| MUW 1138 | 50 + 100 + 2.5 | 5 | 5 | 5 | 5 | 5 | — | — |
| + | 50 + 50 + 5 | 5 | 5 | 5 | 5 | 5 | — | — |
| SK-223 | 50 + 50 + 2.5 | 5 | 5 | 5 | 5 | 5 | — | — |
| + | 25 + 100 + 5 | 5 | 5 | 5 | 5 | 5 | — | — |
| MK-129 | 25 + 100 + 2.5 | 5 | 5 | 5 | 5 | 5 | — | — |
| (invention) | 25 + 50 + 5 | 5 | 5 | 5 | 5 | 5 | — | — |
| | 25 + 50 + 2.5 | 5 | 5 | 5 | 5 | 5 | — | — |
| Non-treated | | 0 | 0 | 0 | 0 | 0 | — | — |

WEED CONTROL EXAMPLE 7

The same procedure as in Weed Control Example 6 was repeated except as noted in Table 7. The results are shown in Table 7.

TABLE 7

| Compound | Dosage g 10a | Herbicidal activity | | | | | Phytotoxicity to rice | |
|---|---|---|---|---|---|---|---|---|
| | | Barnyard grass | Toothcup | Narrowleaf waterplantain | Cyperus sp. | Hard-stem bulrush | Direct sowing | Transplantation |
| MUW 1193 | 50 | 4.5 | 1 | 0 | 1.5 | 1 | — | — |
| (comparison) | 25 | 4 | 0 | 0 | 0 | 0 | — | — |
| MUW 1193 | 50 + 100 | 5 | 3 | 2.5 | 5 | 5 | — | — |
| + | 50 + 50 | 5 | 2.5 | 2 | 5 | 5 | — | — |
| SK-223 | 25 + 100 | 5 | 3 | 1.5 | 5 | 5 | — | — |
| (invention) | 25 + 50 | 5 | 2.5 | 1.5 | 5 | 5 | — | — |
| MUW 1193 | 50 + 5 | 5 | 5 | 5 | 4 | 2.5 | — | — |
| + | 50 + 2.5 | 5 | 5 | 5 | 3.5 | 1 | — | — |
| MK-129 | 25 + 5 | 5 | 5 | 5 | 4 | 2.5 | — | — |
| (invention) | 25 + 2.5 | 5 | 5 | 5 | 3 | 1 | — | — |
| SK-223 | 100 + 5 | 2 | 3.5 | 3 | 5 | 4.5 | — | — |
| + | 100 + 2.5 | 1 | 2 | 2.5 | 4.5 | 4 | — | — |
| MK-129 | 50 + 5 | 2 | 3 | 3 | 4.5 | 4 | — | — |

TABLE 7-continued

| Compound | Dosage g 10a | Herbicidal activity | | | | | Phytotoxicity to rice | |
|---|---|---|---|---|---|---|---|---|
| | | Barnyard grass | Toothcup | Narrowleaf waterplantain | Cyperus sp. | Hard-stem bulrush | Direct sowing | Transplantation |
| (comparison) | 50 + 2.5 | 1 | 1.5 | 2.5 | 4 | 4 | — | — |
| MUW 1193 | 50 + 100 + 5 | 5 | 5 | 5 | 5 | 5 | — | — |
| + | 50 + 100 + 2.5 | 5 | 5 | 5 | 5 | 5 | — | — |
| SK-223 | 50 + 50 + 5 | 5 | 5 | 5 | 5 | 5 | — | — |
| + | 50 + 50 + 2.5 | 5 | 5 | 5 | 5 | 5 | — | — |
| MK-129 | 25 + 100 + 5 | 5 | 5 | 5 | 5 | 5 | — | — |
| (invention) | 25 + 100 + 2.5 | 5 | 5 | 5 | 5 | 5 | — | — |
| | 25 + 50 + 5 | 5 | 5 | 5 | 5 | 5 | — | — |
| | 25 + 2.5 | 5 | 5 | 5 | 5 | 5 | — | — |
| Non-treated | | 0 | 0 | 0 | 0 | 0 | — | — |

As is clearly shown from the test results given hereinabove, the herbicidal compositions of this invention have a broadened herbicidal spectrum against a wide range of weeds from broad-leaved weeds such as toothcup, narrowleaf waterplantain and *Sagittaria pygmaea* and other weeds such as Cyperus sp. without destroying the selectivity of the compound of formula (1) among plants of Family Gramineae. While the compound of formula (1), when applied alone, shows a marked effect only on barnyard grass at the time of emergence to the 1-leaf stage, the herbicidal compositions of this invention can be applied with good results to barnyard grass in the 2-leaf and later stages.

Thus, the compositions of this invention are herbicidal compositions useful for controlling barnyard grass in rice cultivation which have a broadened herbicidal spectrum and an extended period of application, and which have long been desired in the art. These excellent herbicidal compositions were quite unexpected in the past in that such compositions are based on the selectivity of the compound of formula (1) among plants of Family Gramineae, and the compound of formula (1) as ingredient (a), in combination with the ingredient (b), synergistically exhibits a herbicidal effect against broad-leaved weeds and other weeds such as Cyperus sp. in small dosages.

What we claim is:

1. A method for controlling weeds, which comprises applying to the locus where the weeds are growing or will grow, 1 to 2,000 g 10 ares of a mixture of
   (a) an S-α,α-dimethylbenzyl-N-alkylenimine carbothiolate of the formula

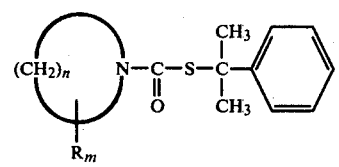

(1)

wherein R represents a lower alkyl group, m is 0, 1 or 2, n is 4, 5 or 6, and the chain of n —CH$_2$— linkages may contain one oxygen atom, and
   (b) 3,4-dichloropropionanilide in a weight ratio of 10 to 400 parts (6) to 100 parts (a).

2. The method of claim 1 wherein said locus is the one where rice is cultivated or will be cultivated.

3. The method according to claim 2 wherein said mixture is applied at a point in time between the germination stage and the initial stage of growth up to the 3.5-leaf stage of the rice plant.

4. The method of claim 1 wherein n=5 in component (a).

5. A herbicidal composition comprising a herbicidal amount of a mixture of
   (a) an S-α,α-dimethylbenzyl-N-alkylenimine carbothiolate of the formula

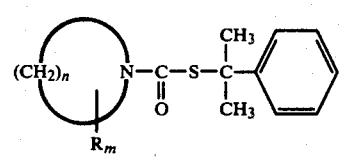

(I)

wherein R represents a lower alkyl group, m is 0, 1 or 2, n is 4, 5 or 6, and the chain of n—CH$_2$—linkages may contain one oxygen atom, and
   (b) 3,4-dichloropropionanilide, and a diluent or carrier, said mixture consisting of 100 parts by weight of the ingredient (a) and 10 to 400 parts by weight of the ingredient (b).

6. The herbicidal composition according to claim 5 wherein n=5 in component (a).

7. The composition of claim 5 wherein the ratio of (a) to (b) is 100 to 400 parts (b) per 100 parts (a).

* * * * *